(12) United States Patent
Wollborg et al.

(10) Patent No.: US 11,707,416 B2
(45) Date of Patent: Jul. 25, 2023

(54) PRESCRIPTION MONITORING SYSTEM

(71) Applicants: Kenan J. Wollborg, Inkster, MI (US); Grady L. Toombs, Esq., Shelby Township, MI (US); Alison Janet Lee, Walled Lake, MI (US); Kevin Richard Lee, Walled Lake, MI (US)

(72) Inventors: Kenan J. Wollborg, Inkster, MI (US); Grady L. Toombs, Esq., Shelby Township, MI (US); Alison Janet Lee, Walled Lake, MI (US); Kevin Richard Lee, Walled Lake, MI (US)

( * ) Notice: Subject to any disclaimer, the term of this patent is extended or adjusted under 35 U.S.C. 154(b) by 429 days.

(21) Appl. No.: 16/852,853

(22) Filed: Apr. 20, 2020

(65) Prior Publication Data

US 2020/0383874 A1 Dec. 10, 2020

Related U.S. Application Data

(60) Provisional application No. 62/836,379, filed on Apr. 19, 2019.

(51) Int. Cl.
| | |
|---|---|
| *A61J 7/04* | (2006.01) |
| *G16H 40/67* | (2018.01) |
| *A61P 25/36* | (2006.01) |
| *G16H 20/13* | (2018.01) |
| *A61J 7/02* | (2006.01) |

(52) U.S. Cl.
CPC ............ *A61J 7/0436* (2015.05); *A61P 25/36* (2018.01); *G16H 20/13* (2018.01); *G16H 40/67* (2018.01); *A61J 7/02* (2013.01); *A61J 2200/74* (2013.01)

(58) Field of Classification Search
CPC ............................... E05G 1/005; B25H 3/023
USPC ................................................ 700/231–244
See application file for complete search history.

(56) References Cited

U.S. PATENT DOCUMENTS

| | | | |
|---|---|---|---|
| 4,275,384 A * | 6/1981 | Hicks | A61J 7/04 340/309.7 |
| 4,899,839 A | 2/1990 | Dessertine et al. | |
| 5,016,172 A | 5/1991 | Dessertine | |
| 5,915,553 A * | 6/1999 | Brown | B25H 3/022 220/521 |
| 6,294,999 B1 | 9/2001 | Yarin et al. | |
| 6,401,994 B1 * | 6/2002 | Ham | B60R 7/14 109/51 |
| 6,539,281 B2 | 3/2003 | Wan et al. | |
| 6,771,174 B2 | 8/2004 | Broas | |
| 7,801,745 B2 | 9/2010 | Walker et al. | |

(Continued)

OTHER PUBLICATIONS

MedSignals medication management system, www.medsignals.com.

*Primary Examiner* — Timothy R Waggoner
(74) *Attorney, Agent, or Firm* — Carlson, Gaskey & Olds, P.C.

(57) ABSTRACT

A monitoring system includes a weight sensor for receiving a vial containing a controlled substance possessed by a patient. A processor receives a weight measured by the weight sensor. A communication circuit transmits the weight measured by the weight sensor to a remote server. The weight sensor may be mounted in a container having a first compartment and a second compartment. The first compartment has a first lid that is releasable without any lock. A second compartment has a second lid that is secured by a lock. The weight sensor is mounted inside the second compartment.

16 Claims, 15 Drawing Sheets

(56) References Cited

U.S. PATENT DOCUMENTS

| | | | |
|---|---|---|---|
| 7,928,825 B2 | 4/2011 | Yang | |
| 7,928,835 B1 | 4/2011 | Jovanov et al. | |
| 8,069,056 B2 | 11/2011 | Walker et al. | |
| 8,108,068 B1* | 1/2012 | Boucher | G01G 17/00 |
| | | | 700/240 |
| 8,267,247 B1* | 9/2012 | Horiyama | B25H 3/025 |
| | | | 220/843 |
| 8,636,516 B2 | 1/2014 | Batsikouras | |
| 8,770,983 B2 | 7/2014 | Batsikouras | |
| 2002/0027507 A1 | 3/2002 | Yarin et al. | |
| 2002/0067270 A1 | 6/2002 | Yarin et al. | |
| 2006/0276931 A1 | 12/2006 | Walker et al. | |
| 2009/0134181 A1 | 5/2009 | Wachman et al. | |
| 2010/0283601 A1 | 11/2010 | Tai et al. | |
| 2014/0310018 A1* | 10/2014 | Cizmarik | G16H 40/40 |
| | | | 705/2 |
| 2015/0310185 A1* | 10/2015 | Shah | A61J 7/0454 |
| | | | 340/10.6 |
| 2016/0015602 A1* | 1/2016 | Panzini | A61J 7/0481 |
| | | | 206/534 |
| 2016/0026773 A1* | 1/2016 | Chu | G01L 5/00 |
| | | | 705/2 |
| 2017/0074717 A1* | 3/2017 | Pilkington | G01G 19/4144 |
| 2018/0064609 A1* | 3/2018 | Hines | G16H 40/67 |
| 2018/0078200 A1* | 3/2018 | Bowline | A61J 1/035 |

* cited by examiner

Commission and Load — 220

- Logout
- Commission
- Alert

- Box ID — 222
- Device Phone — 224
- Doctor/Contact Info — 228, Filter — 226
- Text Alert Number — 230
- Commission Date: 04-12-2019
- Technician — 232 (25 characters, no quote marks)

- Scale 1 fill count
- Scale 2 fill count
- Scale 3 fill count
- Scale 4 fill count
— 240

SMS ID empty bottles — 244

- Scale 1 max daily pill use
- Scale 2 max daily pill use
- Scale 3 max daily pill use
- Scale 4 max daily pill use
— 242

SMS ID loaded bottles — 246

Fill out above fields, click to [Add Data]
Delete all from commission database [Delete]
Clear form [Cancel]

FIG. 14A

| SMS ID | Phone | Scale #1 | #2 | #3 | #4 | Date |
|---|---|---|---|---|---|---|
| 303 | +1313999XXXX | 159.47 | 188.10 | 85.54 | 30.93 | 03-22-2019 |
| 302 | | 159.57 | 188.07 | 85.60 | 30.87 | |
| 301 | | 47.66 | 188.19 | -0.36 | 0.22 | |
| 300 | | 47.58 | 188.10 | -0.44 | 0.22 | |
| 299 | | 47.64 | 188.06 | -0.41 | 0.30 | |
| 298 | | 47.62 | 188.07 | -0.35 | 0.21 | |
| 297 | | 47.60 | 188.15 | -0.35 | 0.35 | |
| 296 | | 47.56 | 0.07 | -0.42 | 0.41 | |
| 295 | | 51.20 | 0.05 | -0.27 | 0.45 | |
| 294 | | 51.24 | 0.05 | -0.26 | 0.54 | |

| Device Phone | CommissionDate | BoxID | ContactInfo | AlertNumber | Commissioner | ProductWt1 | FillCount1 | MaxUse1 |
|---|---|---|---|---|---|---|---|---|
| +1313999XXXX | 03-08-2019 | 123 Me | | +1313888XXXX | Bob | 24.730 | 20 | 6 |

FIG. 14B

PRESCRIPTION MONITORING SYSTEM

BACKGROUND

Medication non-adherence by patients leads to ineffective treatments, unnecessary suffering, worsening disease processes, and possibly death. Non-adherence is a highly prevalent problem; approximately 50%-60% of patients do not take their prescribed medications as directed which contributes significantly to healthcare costs per year for hospitalizations alone. Medication adherence is both critically important and particularly challenging in the case of opioid analgesics where misuse can lead to opiate addiction, overdoses, and death, posing risks not only to the individual, but also the community.

Opioids are frequently used in chronic pain management and can be the only agents capable of providing relief. Due to the high prevalence of chronic pain and the cultural shift to address uncontrolled pain that began in the early 1990s the consumption of prescription opioids in the US has grown dramatically.

Aberrant drug-related behaviors associated with prescription opioids include drug abuse (intentional self-administration of a medication for a nonmedical purpose), addiction, and diversion (intentional transfer of a controlled substance from legitimate distribution and dispensing channels). These behaviors not only harm the affected individual, but also come at a high societal cost.

These behaviors and their consequences can be mitigated by closely monitoring medication adherence and by rapid interventions when non-adherence is detected. Early implementation of adherence testing for opioids has been shown to improve patient outcomes and to reduce healthcare costs. However, the inherently high potential for abuse and addiction of opioid medication makes medication management a formidable task, as patients actively attempt to conceal their nonadherence, which excludes self-report measures such as patient-kept diaries and interviews. Traditionally employed periodic pill counts that assess patient compliance by comparing the number of pills in a vial at a random time to the number of pills that should remain in the vial have been shown to be circumvented by patient manipulation including "pill rentals" from illegal sources that satisfy periodic pill counts for a fee. Furthermore, in case of medications such as opioids, a monthly evaluation of adherence is not sufficiently frequent, as it allows for extended periods of misuse.

SUMMARY

A monitoring system includes a weight sensor for receiving a vial containing a controlled substance possessed by a patient. A processor receives a weight measured by the weight sensor. A communication circuit transmits the weight measured by the weight sensor to a remote server.

The weight sensor may be mounted in a container having a first compartment and a second compartment. The first compartment has a first lid that is releasable without any lock. A second compartment has a second lid that is secured by a lock. The weight sensor is mounted inside the second compartment.

BRIEF DESCRIPTION OF THE DRAWINGS

FIG. 14A is a first portion of a commissioning screen.

FIG. 14B is a second portion of a commissioning screen.

DETAILED DESCRIPTION

Figure 1:
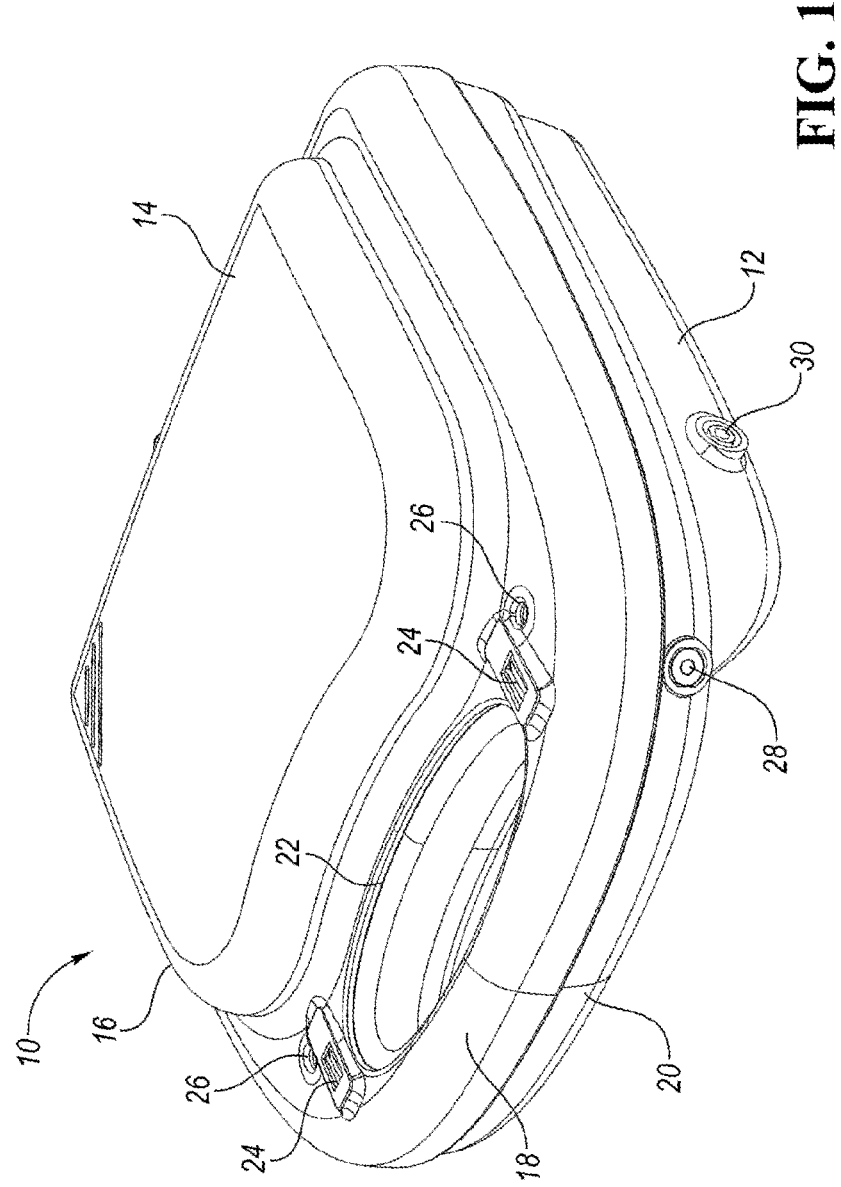
FIG. 1 is a front perspective view of a container according to one embodiment.

A prescription monitoring system or drug monitoring system includes a lockable container 10 shown in FIG. 1. The container 10 includes a lower base portion 12 and an upper lid 14. The upper lid 14 includes an upper compartment 16. The upper lid 14 further includes a handle portion 18 which mates with a handle portion 20 of the lower base portion 12 to form a handle for the container 10.

A handle opening 22 through the upper lid 14 is formed between the handle portion 18 and the upper compartment 16. A pair of latches 24 secures the upper lid 14 in the closed position. The latches 24 can be selectively released to open the upper lid 14 without a key. A pair of indicators 26 are visible through openings in the upper lid 14.

The lower base portion 12 includes an opening for a lock 28 operated via a key. The lower base portion 12 also includes an opening for a power supply jack 30.

Figure 2:
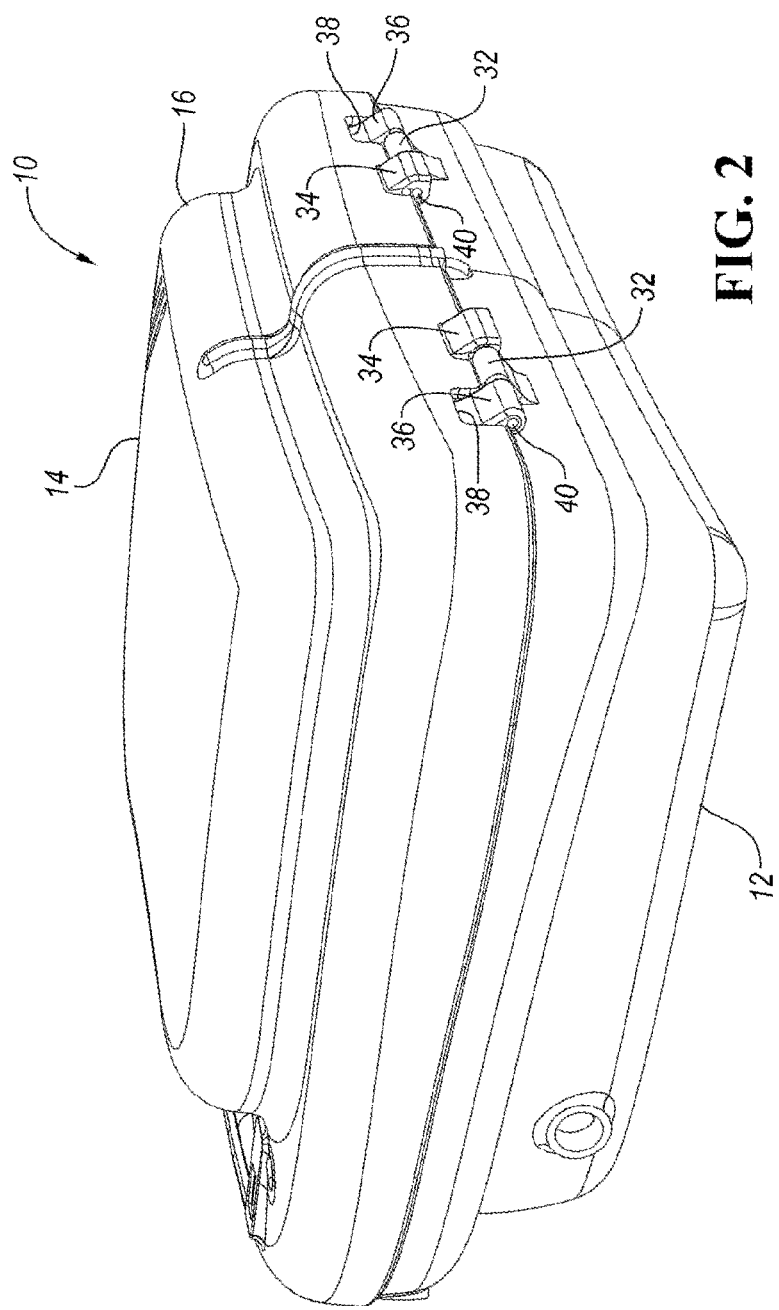
FIG. 2 is a rear perspective view of the container of FIG. 1.

FIG. 2 is a rear perspective view of the container 10. The lower base portion 12 includes a pair of integrally molded hinge receivers 32. Likewise the upper lid 14 includes a pair of integrally molded hinge receivers 34 positioned adjacent the hinge receivers 32 of the lower base portion 12. Further, a pair of notches 38 are formed in the rear of the upper lid 14 for receiving hinge receivers 36 of an inner cover (described below). Hinge pins 40 pivotably connect the hinge receivers 32, 34, 36. Alternatively, other complementary hinge members or hinge components other than hinge receivers 32, 34, 36 could hingeably connect to one another.

Figure 3:
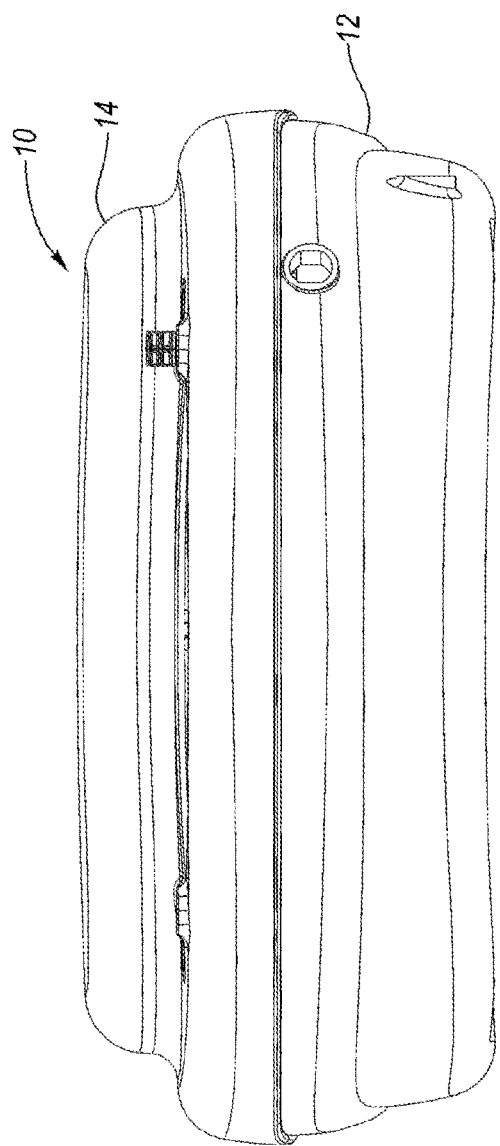
FIG. 3 is a front view of the container of FIG. 1.
Figure 4:
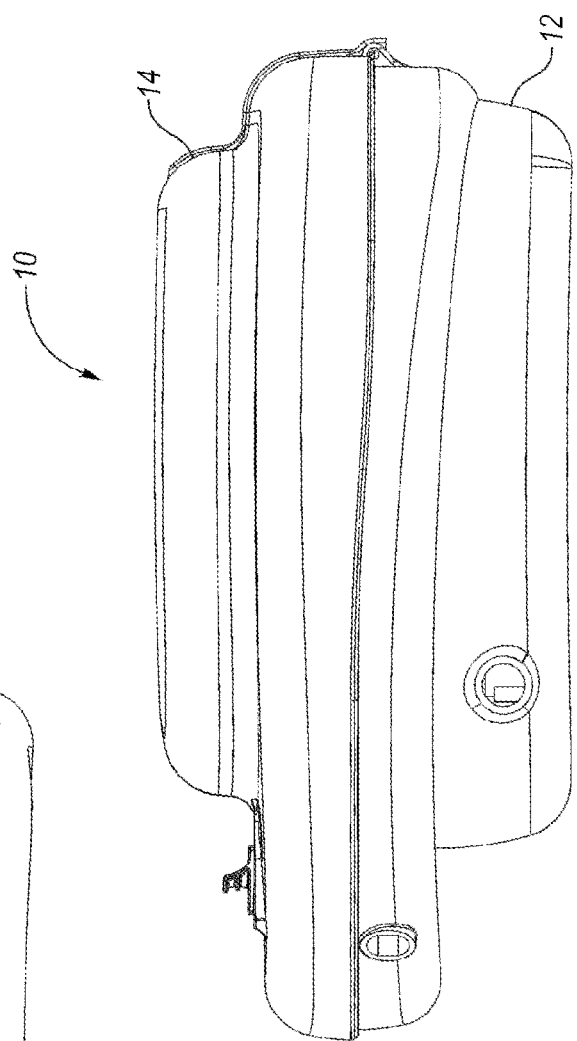
FIG. 4 is a side view of the container of FIG. 1.

FIG. 3 is a front view of the container 10. FIG. 4 is a side view of the container 10.

Figure 5:
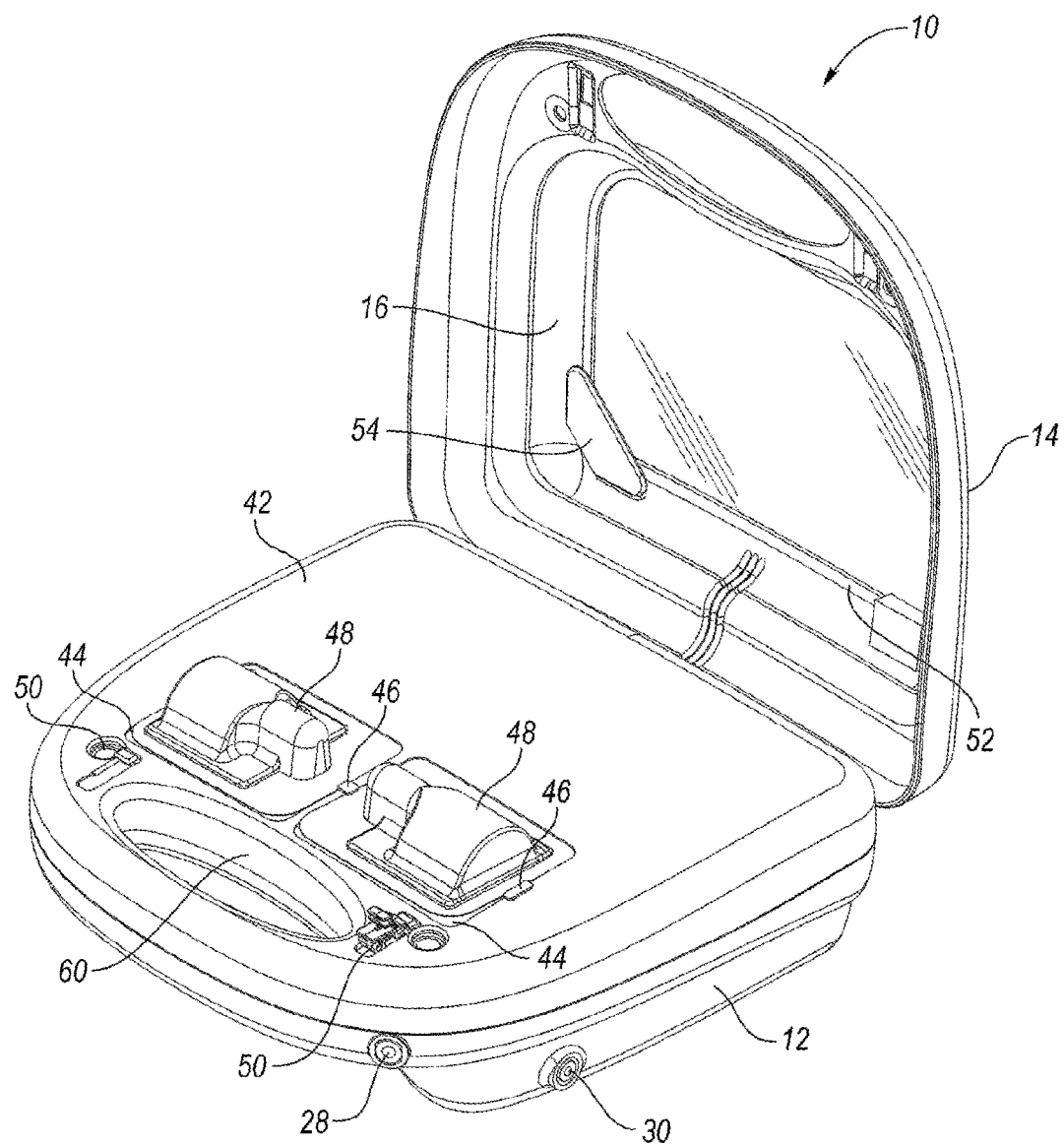
FIG. 5 is a front perspective view of the container of FIG. 1 with the upper lid open.

FIG. 5 is a perspective view of the container 10 with the upper lid pivoted to the open position. The inner cover 42 (or inner lid) covers the base and is secured to the base by the lock 28. A pair of recesses 44 are formed in an upper surface of the inner cover 42. Clips 46 adjacent the recesses 44 removably secure packages 48, which may contain emergency supplies, such as naloxone.

Latch members 50 on the inner cover 42 selectively secure the inner cover 42 to the latches 24 (FIG. 1) of the upper lid 14. The upper lid 14 can always be unlatched without a key, to provide access to the packages 48 of the emergency supplies.

A mobile computing device 52, such as a tablet, is secured within the upper compartment 16 of the upper lid 14 and is secured to the upper lid 14 by brackets 54 and/or clips. As is known, the mobile computing device 52 includes a processor, electronic storage, communication circuitry, such as Wi-Fi, Bluetooth, and cell circuitry. The mobile computing device 52 also includes a GPS receiver, touch screen display, microphone, and speaker. The mobile computing device 52 includes a battery that is rechargeable via the power supply jack 30.

The inner cover 42 includes an elliptical wall 60 projecting downward to further define the handle of the container 10.

Figure 6:
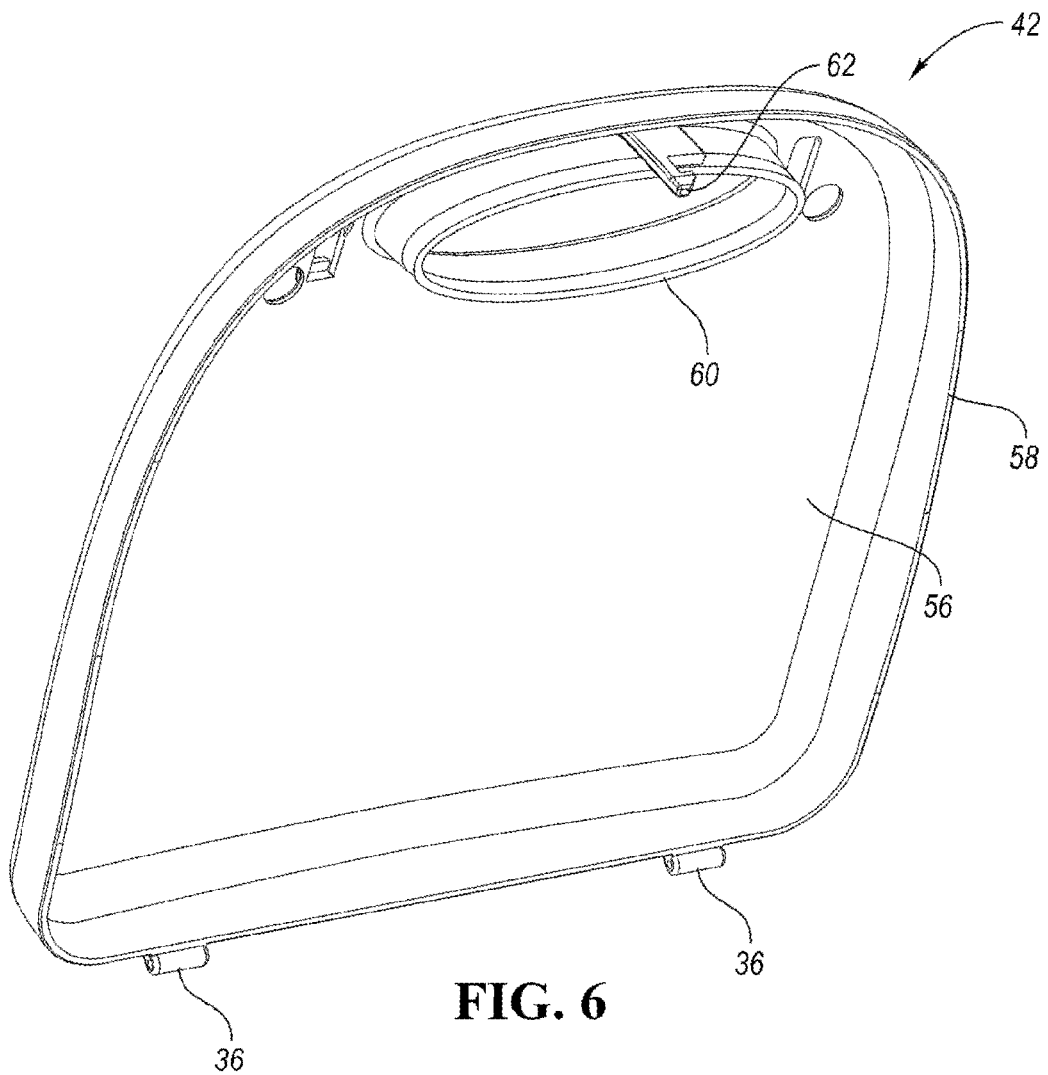
FIG. 6 is a bottom perspective view of the inner cover of the container of FIG. 5.

FIG. 6 is a bottom perspective view of the inner cover 42. The inner cover 42 includes an upper panel portion 56 and peripheral wall 58 projecting downward from the upper panel portion 56. The hinge receivers 36 are integrally molded with the peripheral wall 58 at a rear portion of the inner cover 42. A latch member 62 projects downward from the inner cover 42 between the peripheral wall 58 and the elliptical wall 60. The latch member 62 is selectively securable to the lower base portion 12 by the lock 28 (FIG. 1).

Figure 7:
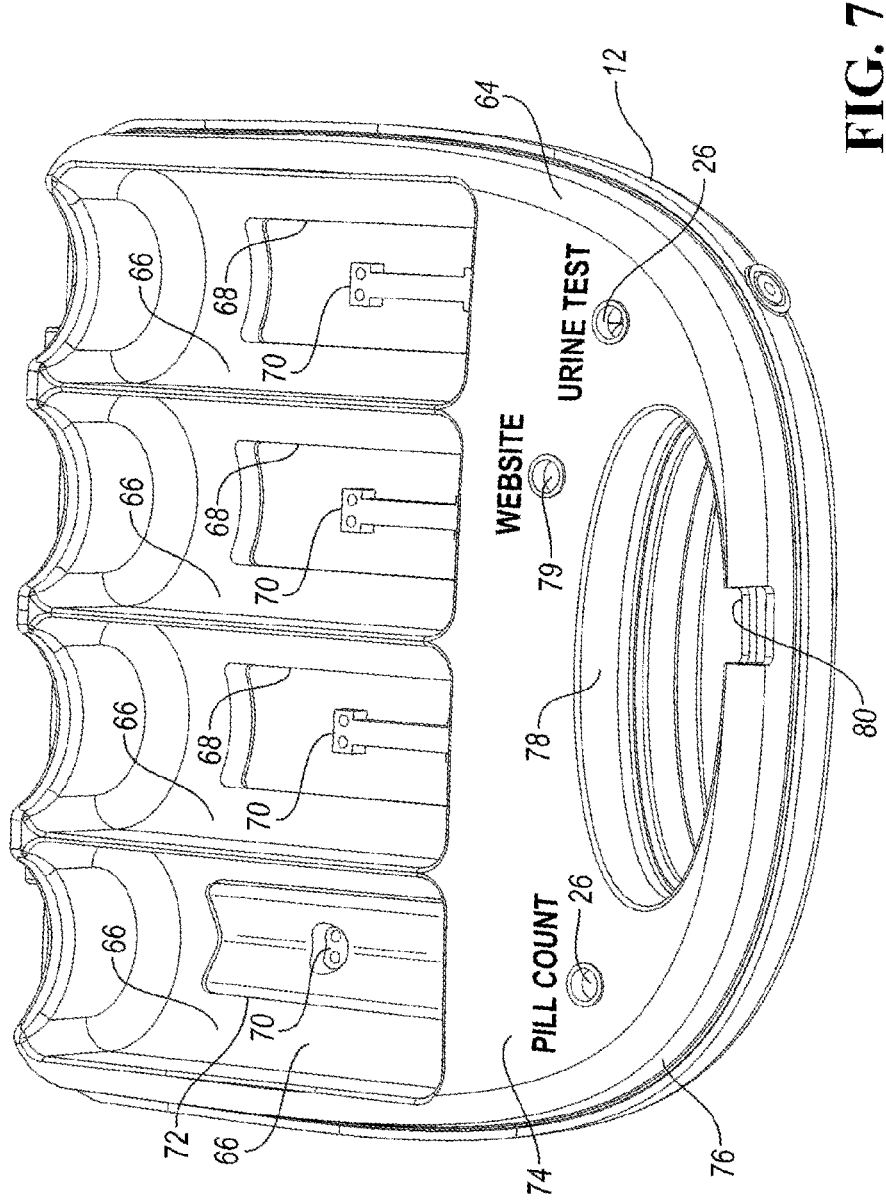
FIG. 7 shows the base portion of the container of FIG. 1 with the upper lid and inner cover removed.

In FIG. 7, the upper lid 14 and inner cover 42 have been removed to show an upper base portion 64 secured to the lower base portion 12. The upper base portion 64 includes a lower compartment having a plurality of bays 66 defined therein (in this example there are four bays 66, although more or fewer could be provided). Each bay 66 includes an opening 68 at the bottom thereof. A weight sensor 70 is secured to the lower base portion 12 within each opening 68 in each bay 66. A cradle 72 is secured to each weight sensor 70 over each opening 68 within each bay 66. In FIG. 7, only one cradle 72 is shown, while the others are removed for illustration.

The upper base portion 64 includes an upper wall 74 having a peripheral wall 76 extending downward from a periphery of the upper wall 74 and mating with the lower base portion 12. An elliptical handle wall 78 projects downward from the upper wall 74 of the upper base portion 64 to further define the handle. An opening 80 is formed through the upper wall 74 forward of the handle portion to receive the latch member 62 of the inner cover 42 (FIG. 6). The indicators 26 (such as LEDs) are secured within apertures in the upper wall 74 of the upper base portion 64. In the example shown, the indicators are labeled "pill count" and "urine test" on the upper wall 74 of the upper base portion 64. A "website" button 79 can let the user or technician provide various acknowledgments to the system, such as acknowledging that the user has seen one of the indicators 26 activated (it can be deactivated in the meantime after the user acknowledges it).

Figure 8:
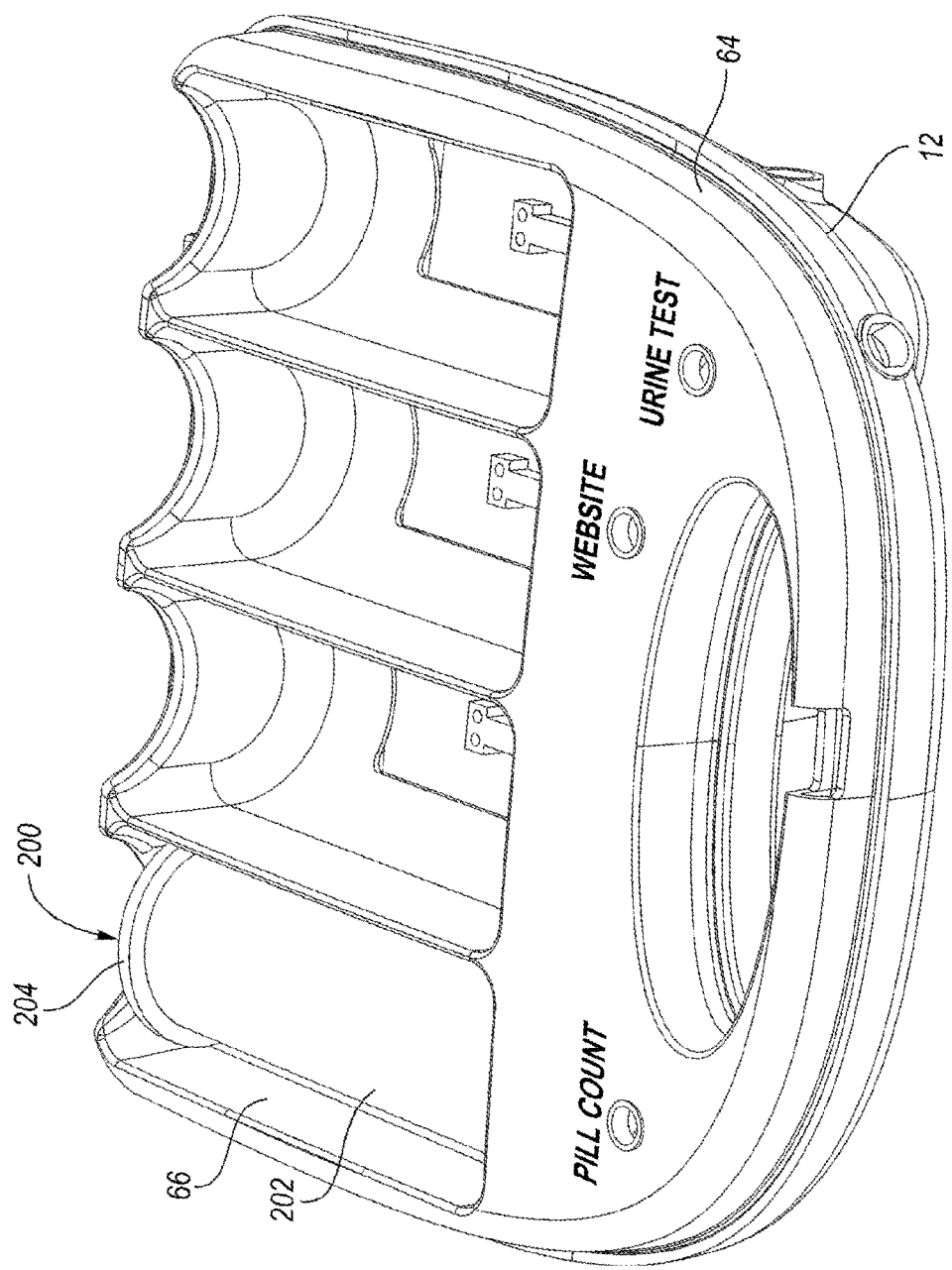
FIG. 8 shows base portion of FIG. 7, with a vial stored in one of the bays.
Figure 9:
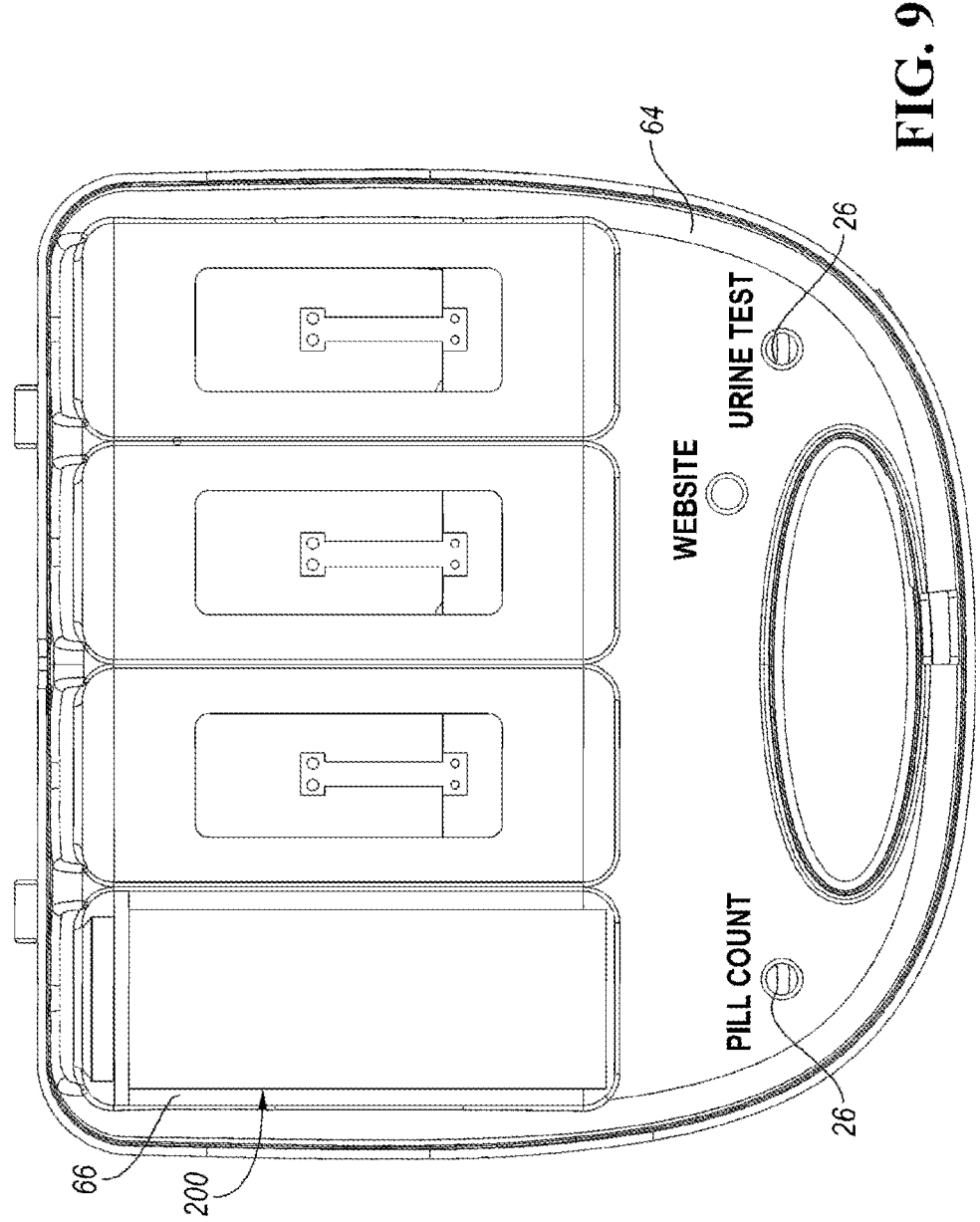
FIG. 9 is a top view of the base portion and vial of FIG. 8.

FIG. 8 shows the lower base portion 12 and upper base portion 64 of FIG. 7, with a vial 200 stored in one of the bays 66. The vial 200 in this example includes a generally cylindrical wall 202 and a removable lid 204. Identical vials 200 could be received in the other bays 66. FIG. 9 is a top view of the upper base portion 64 and vial 200 of FIG. 8.

Figure 10:
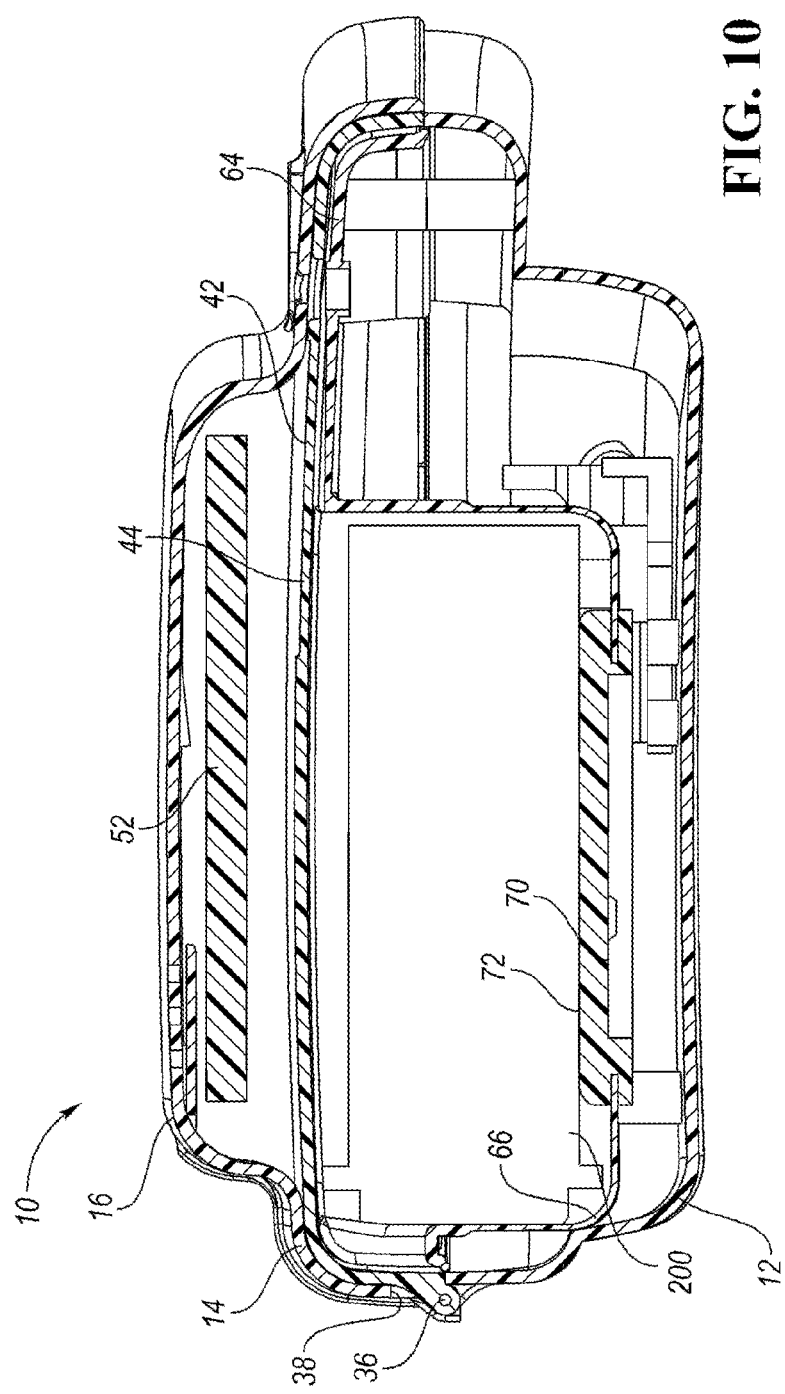
FIG. 10 is a section view of the container of FIG. 1 with the vial.

FIG. 10 is a section view of the container 10 and vial 200. As shown, the vial 200 is supported on the cradle 72, which in turn is supported on the weight sensor 70. All of the weight of the vial 200, any contents therein, and cradle 72 are supported on the weight sensor 70. The weight sensor 70 reports its weight measurements to the mobile computing device 52 either wirelessly or through wires (not shown).

The inner cover 42 is secured over the upper base portion 64. The inner cover 42 is secured to the lower base portion 12 at a rearward end by the hinge receiver 36. In FIG. 10, the emergency supplies 48 are not shown, although the recess 44 in the inner cover 42 can be seen. The mobile computing device 52 is stored in the upper compartment 16 of the upper lid 14.

Figure 11:
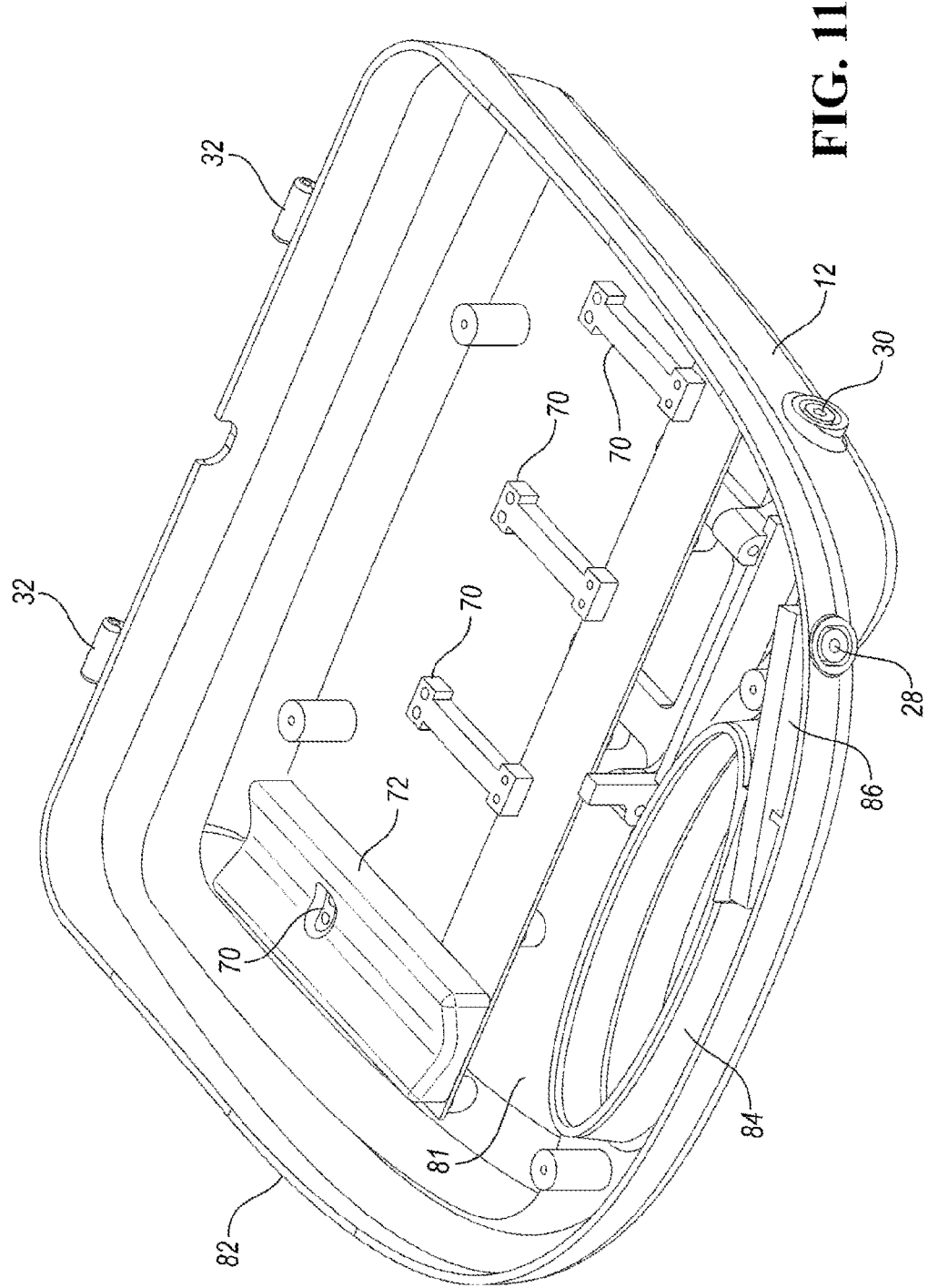
FIG. 11 is a perspective view of the lower base portion of FIG. 7.
Figure 12:
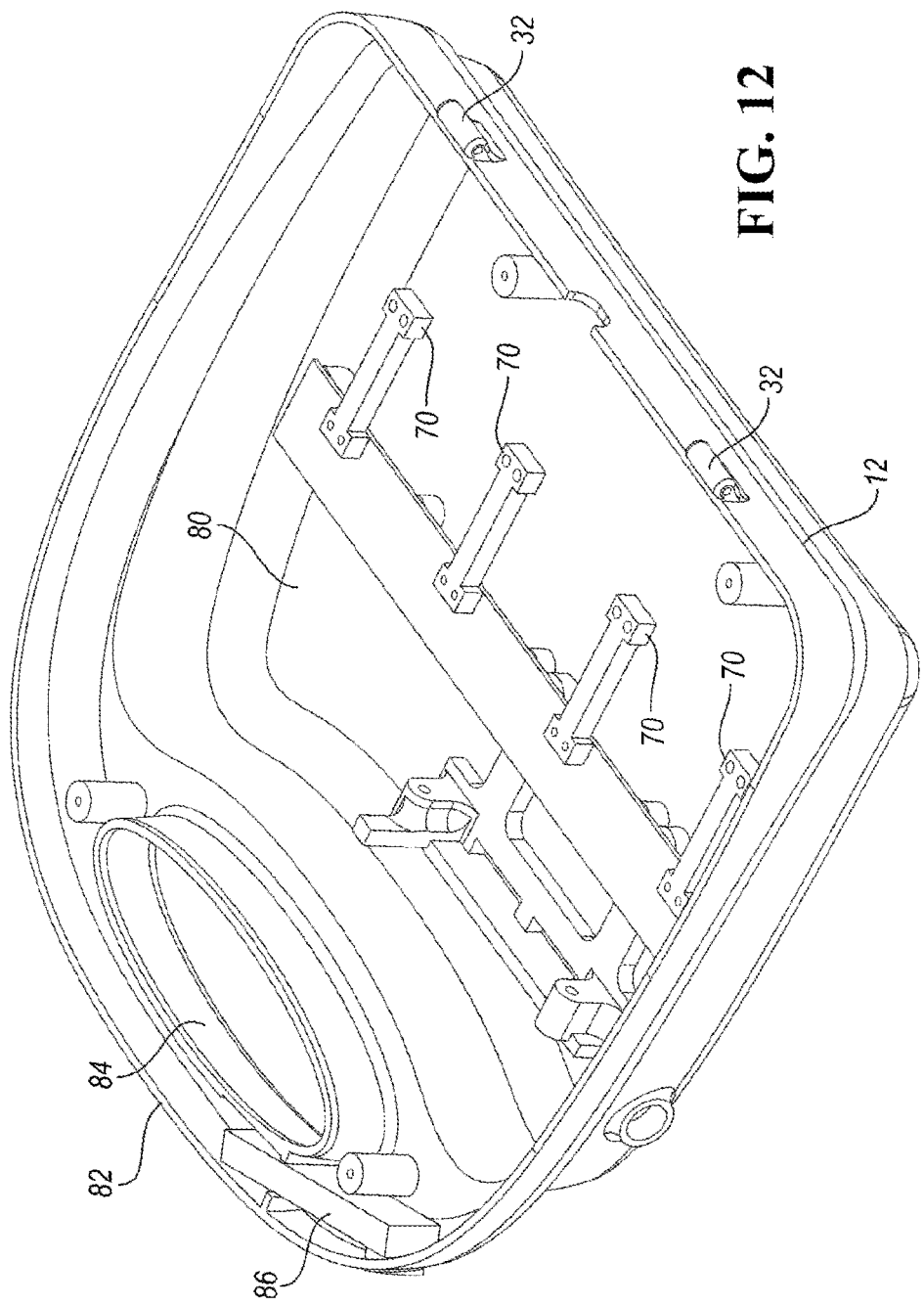
FIG. 12 is a rear perspective view of the lower base portion of FIG. 11, without the cradle.

FIG. 11 is a perspective view of the lower base portion 12. Again, a plurality of weight sensors 70 are secured to the lower base portion 12. A cradle 72 is secured to each weight sensor 70 (although only one cradle 72 shown). A locking latch 86 is secured to the lower base portion 12 for latching to the latch member 62 of the inner cover 42 (FIG. 6) and releasable via a key in the lock 28. The lower base portion 12 includes an elliptical handle wall 84 further defining the handle opening. The lower base portion 12 further includes a lower wall 81 and a peripheral wall 82 extending upward of a periphery of the lower base portion 12. The hinge receivers 32 are integrally molded with the peripheral wall 82. FIG. 12 is a rear perspective view of the lower base portion 12 of FIG. 11, without the cradle 72.

Figure 13:
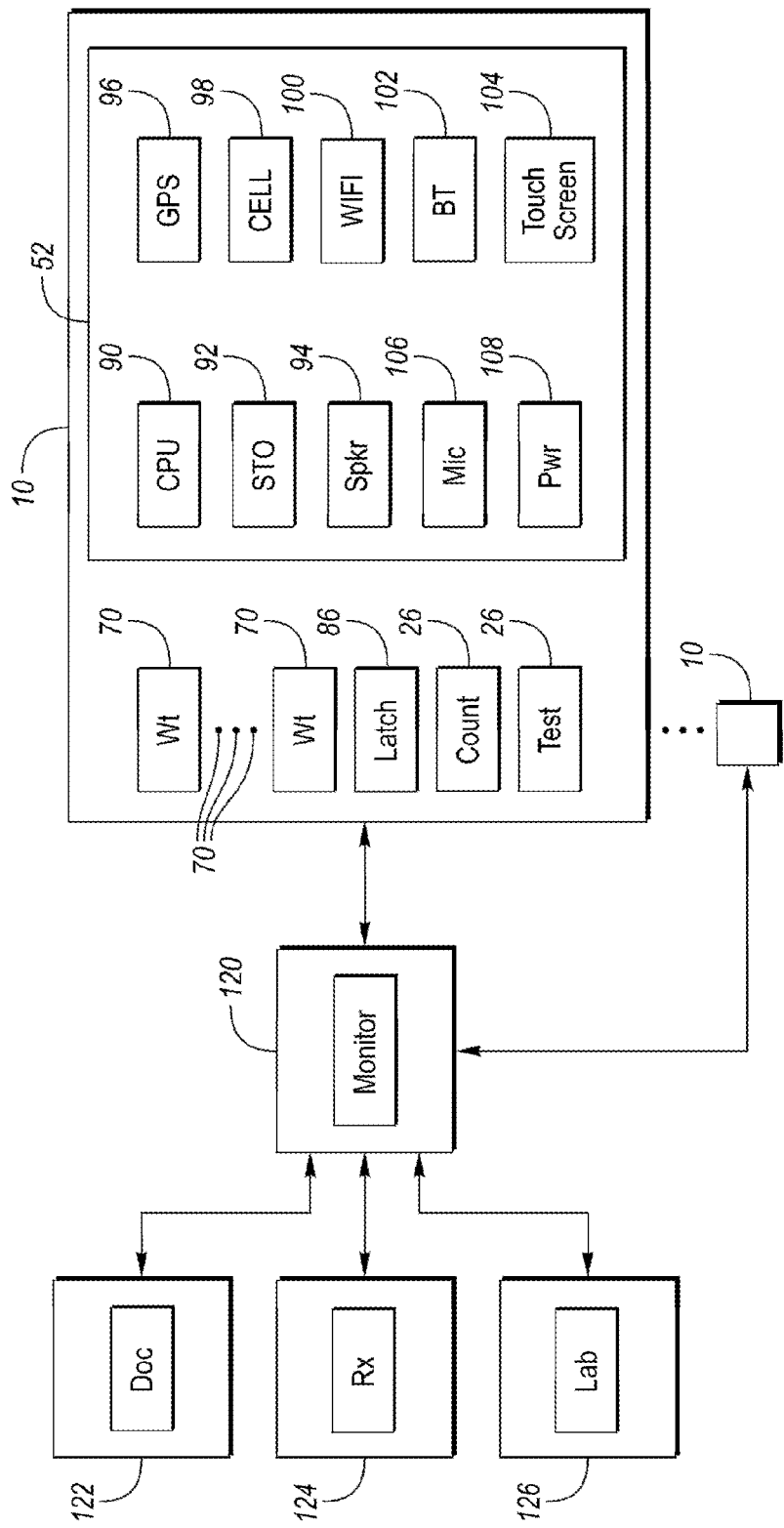
FIG. 13 is a schematic of a monitoring system including a plurality of the containers.

FIG. 13 is a schematic of a monitoring system 8 including a plurality of the containers 10. As explained above, each container 10 includes the mobile computing device 52 in communication with the plurality of weight sensors 70, the latch 86, and the indicators 26. The mobile computing device 52 is capable of releasing the latch 86 and is notified when the latch 86 is manually unlocked and the lid 14 is opened. The mobile computing device 52 can activate and deactivate the indicators 26. The mobile computing device 52 receives the measurement signals from the weight sensors 70 and input from the website button 79 (FIG. 7).

The mobile computing device 52 may be a tablet or smartphone, which as is known includes a processor 90, electronic storage 92, communication circuitry such as Wi-Fi 100, Bluetooth 102, and cell circuitry 98. The mobile computing device 52 also includes a GPS receiver 96, touch screen display 104, microphone 106, and speaker 94. The mobile computing device 52 includes a battery 108 that is rechargeable via the power supply jack 30. The processor 90 is programmed (via an app stored in electronic storage 92) to perform the functions described herein.

The mobile computing device 52 communicates wirelessly (via cell circuitry 98, Wi-Fi 100, and/or Bluetooth 102 or the like) over the Internet or other network with a monitoring server 120 (which could be one or more virtual and/or physical servers). The monitoring server 120 is suitably programmed to perform the functions described herein. The monitoring server 120 is also in communication with a doctor computer 122, a pharmacy computer 124, and a lab computer 124, via a network, such as the Internet, or any appropriate entity capable of communicating via any of the above methods.

In general operation, a patient is issued the container 10 with one or more vials 200 each containing a prescription, such as a controlled substance, such as an opioid or other prescribed medication. The container 10 (more specifically, the mobile computing device 52) monitors the opening and closing of the inner cover 42 (by monitoring latch 86) to initiate a measurement of the weight of each vial 200 using the weight sensors 52. The measured weights of the vials 200 are sent by the mobile computing device 52 via the cell circuitry 96, Wi-Fi 100, Bluetooth 102, or the like. Every time a vial 200 is removed, that weight sensor 70 is recalibrated (rezeroed) while that vial 200 is absent. When the vial 200 is replaced on the cradle 72, the weight of the vial 200 (and any contents) is measured again after the inner cover 42 is closed and the new weight measurement is then transmitted by the mobile computing device 52. The measurements from all of the weight sensors 70 may be sent (e.g. via SMS) every time the inner cover 42 is closed. Alternatively, only the new weight for the vial 200 that was removed and replaced will be sent. The container 10 may also send its GPS location (from GPS receiver 96).

A doctor can prescribe a controlled substance (such as an opioid or other prescribed medication) and the container 10 for the patient to use. The prescription may include a number of random urine tests to require and/or a number of pill counts to require. The prescription indicates the number of pills the patient should take daily as well as a max number of pills that can be taken daily without triggering an alarm. The doctor can monitor the patient's use of the container 10, the consumption of prescribed medications, and the patient's compliance with any urine tests or pill counts that have been required on the doctor's computer 122, such as via a web browser accessing the monitoring server 120.

A commissioning screen 220 is shown in FIGS. 14A and 14B. This commissioning screen 220 would appear on a computer at a pharmacy where the prescription(s) to be placed in the vial(s) 200 is filled. The commissioning screen 200 may appear on a web browser or a dedicated application, for use by a technician for purposes of sending information to the monitoring server 120. A box ID field 222 is used to enter an identifier for the particular container 10 to be commissioned. A phone number is entered in the device phone field 224, such as the phone number associated with the cell circuitry 98. A doctor/contact info field 226 can be used to enter information regarding how to contact the patient's doctor. A text alert number field 228 can be entered for automated alerts to be sent based upon information from the container 10. The commissioning screen 220 further includes a commission date field 230 and technician field 232 to indicate when and who is commissioning the container 10.

The technician enters the initial number of pills placed in each vial 200 at the pharmacy in the fill count fields 240. The technician also enters values in each max daily pill use 242 field, each associated with one of the vials 200.

The technician can also fills an SMS ID empty bottles field 244 and an SMS ID loaded bottles field 246.

The technician first indicates to the monitoring server 120 via computer 124 that the container 10 is being commissioned. The technician inputs information obtained via a physician's prescription into the monitoring server 120 via computer 124, identifying the action that is to be taken if the amount of pills removed exceeds the weight threshold. The technician then places the empty vials 200 on the weight sensors 70 and pushes the website button 79. The weights of the empty vials 200 are transmitted to the monitoring server 120. The technician then places the filled vials 200 on the weight sensors 70 and pushes the website button 79 again. This causes the weights of the filled vials 200 to be transmitted to the monitoring server 120. When the technician closes the inner cover 42, commissioning mode is ended.

With the empty vial weights, the filled vial weights, and the number of pills in each vial 200, the monitoring server 120 calculates the weight of each pill. The monitoring server 120 also calculates the maximum weight change that can occur within 24 hours for each vial 200, based also upon the max daily pill use fields 242.

A data portion 248 of the commissioning screen 200 shows a sample of data received from the container 10. Each data transmission received from the mobile computing device 52 in the container 10 (e.g. each SMS message) includes an SMS ID 250, which may simply identify each data transmission sequentially. Each data transmission may further include the phone number 254 of the transmitting mobile computing device 52 (associated with a particular container 10). Each data transmission further includes a weight measurement 252 from each weight sensor 70 (FIG. 13) and the date 256 (and time) of the data transmission. This data is received by the monitoring server 120 and may be displayed to the technician on the commissioning screen 220 as shown.

The container 10 with filled vials 200 is given to the patient. Normally, the mobile computing device 52 is in a semi-powered state waiting for the inner cover 42 to be opened (as detected via latch 86). The mobile computing device 52 also monitors external power (via power supply jack 30) and may send an alert message if external power is not connected for a certain amount of time.

To open the inner cover 42 and access the prescriptions in the vials 200, the patient must use a key to unlock the lock 28. When the inner cover 42 is opened, all commissioned weight sensors 70 are monitored by the mobile computing device 52 for weight change. When it is detected that the vial 200 is removed, that weight sensor 70 is re-zeroed. When the vial 200 is returned to the weight sensor 70, the new weight is measured by weight sensor 70 and transmitted to the monitoring server 120.

The monitoring server 120 receives the weight measurements and calculates how many of the pills in each vial 200 are being removed each day. If the amount of pills removed exceeds the threshold associated with that vial 200, then an alert can be sent to the doctor and/or pharmacist and/or the number in the text alert number field 228. The doctor and/or pharmacist may respond by requiring a pill count and/or urine test or in the alternative there will be an automated response generated for a weight threshold violation or for a random alert notice.

At all times, anyone can open the upper lid 14 and retrieve the emergency supplies, such as naloxone, and administer them to the patient.

At all times, the mobile computing device 52 can receive a message (e.g. SMS) from the patient, the monitoring server 120, or the doctor's computer 122 indicating to the mobile computing device 52 to unlock the lock 28, so that the inner cover 42 can be opened. The mobile computing device 52 can also receive a message (e.g. SMS) instructing the mobile computing device 52 to illuminate either the pill count indicator 26 or the urine test indicator 26. After being illuminated, either indicator 26 will turn back off five minutes after the inner cover 42 is opened. When the patient sees the pill count indicator 26 illuminated, then the patient must bring the container 10 to the pharmacy (or doctor or lab) within a certain period of time (e.g. 24 hrs). When the patient sees the urine test indicator 26 illuminated, then the patient must obtain a urine test within a certain period of time (e.g. 24 hrs) at the lab. The lab technician can indicate compliance/noncompliance, and the results of the urine test on the lab computer 126, such as via a web browser accessing the monitoring server 120 and/or direct communications back to the doctor.

Figure 15:
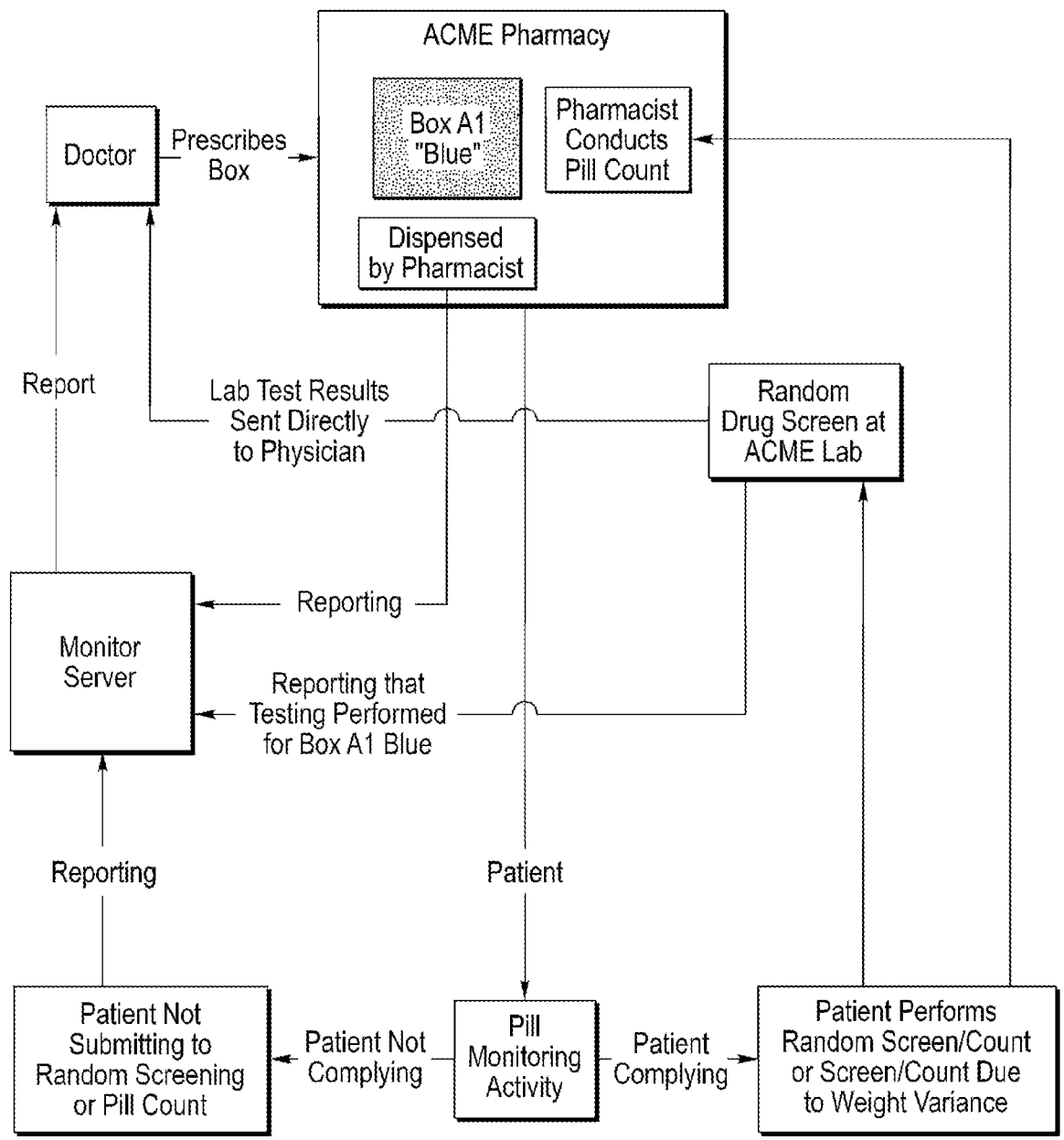
FIG. 15 is an operational flowchart of the monitoring system.

FIG. 15 is an operational flowchart of the monitoring system 8.

Notably, the mobile computing device 52 is generally transmitting weights and time/day (and optionally GPS location). The thresholds, calculations, data, determinations, and alerts are all on the monitoring server 120.

The components of the container 10 housing, i.e. the lower base portion 12, the upper base portion 64, the inner cover 42 and the upper lid 14 are all preferably formed of a suitable molded plastic; however, other materials (such as metal) could also be used for one or more of these components.

The container 10 has been described with the mobile computing device 52 providing all of the intelligence and communication circuitry. Alternatively, cell circuitry and a battery can be provided to simple control circuitry in the container 10 to provide the functions described above, including sending text messages with the weight measurements, receiving signals to turn on one or more indicators 26, unlocking the lock in response to a text message, sending a text message based upon the container 10 being unlocked by the user, etc. The control circuitry may include a processor with electronic storage.

In accordance with the provisions of the patent statutes and jurisprudence, exemplary configurations described above are considered to represent a preferred embodiment of the invention. However, it should be noted that the invention can be practiced otherwise than as specifically illustrated and described without departing from its spirit or scope.

What is claimed is:

1. A container comprising:
   a base;
   a first compartment, wherein the first compartment has a first lid that is releasable without any lock, wherein the first compartment contains naloxone;
   a second compartment, wherein the second compartment has a second lid that is secured by a lock, the second compartment defined between the base and the second lid, wherein the second compartment contains an opioid, wherein the first compartment is defined between the first lid and the second lid; and
   at least one weight sensor within the second compartment each configured to receive a vial thereon.

2. The container of claim 1 wherein the at least one weight sensor is a plurality of weight sensors.

3. The container of claim 1 wherein the base includes at least one bay defined therein, each of the at least one bays having one of the at least one weight sensors therein.

4. The container of claim 3 further including a processor and a communication circuit, wherein the processor is programmed to transmit a weight determined by the at least one weight sensor of the vial received thereon to a remote server.

5. The container of claim 4 wherein the processor is programmed to transmit the weight to the remote server based upon the second lid being closed.

6. The container of claim 1 wherein the first lid and the second lid are hingeably connected directly to the base.

7. The container of claim 6 further including a handle opening formed through the second lid and the base.

8. The container of claim 6 further including a handle opening formed through the first lid and the base.

9. The container of claim 1 wherein the base includes a lower base portion secured to an upper base portion, wherein the upper base portion includes a plurality of bays formed therein, wherein the at least one weight sensor is a plurality of weight sensors, each of the plurality of bays having one of the plurality of weight sensors therein.

10. The container of claim 9 further including at least one indicator formed in the upper base portion.

11. The container of claim 9 wherein the plurality of bays are each configured to receive a vial horizontally therein.

12. The container of claim 1 further including a handle opening formed through the second lid and the base.

13. The container of claim 1 further including a handle opening formed through the first lid and the base.

14. A container comprising:
    a base;
    a first compartment, wherein the first compartment has a first lid that is releasable without any lock;
    a mobile device secured to the first lid;
    a second compartment, wherein the second compartment has a second lid that is secured by a lock, the second compartment defined between the base and the second lid, wherein the first compartment is defined between the first lid and the second lid; and
    at least one weight sensor within the second compartment each configured to receive a vial thereon.

15. A method for monitoring a drug in possession of a patient including:
    a) receiving an indication at a remote server that the container as claimed in 14 is being commissioned;
    b) receiving at the remote server an initial number of pills placed in each of a plurality of vials;
    c) receiving at the remote server a max daily pill use for each of the plurality of vials;
    d) receiving weights of each of the plurality of vials empty;
    e) receiving weights of each of the plurality of vials filled with pills;
    f) after steps a) to e), weighing the drug in the possession of the patient;
    g) reporting the weight to the remote server;
    h) at the remote server, comparing the reported weight to a previously reported weight; and
    i) based upon step h), determining whether to generate an alert.

16. The method of claim 15 wherein in step d), the weights of the vials empty are received from the container.

* * * * *